United States Patent
Czupalla

(10) Patent No.: US 11,278,196 B2
(45) Date of Patent: Mar. 22, 2022

(54) IMAGING MEDICAL INSTRUMENT SUCH AS AN ENDOSCOPE, EXOSCOPE OR MICROSCOPE

(71) Applicant: Karl Storz SE & Co. KG, Tuttlingen (DE)

(72) Inventor: Christian Czupalla, Tuttlingen (DE)

(73) Assignee: Karl Storz SE & Co. KG, Tuttlingen (DE)

( * ) Notice: Subject to any disclaimer, the term of this patent is extended or adjusted under 35 U.S.C. 154(b) by 0 days.

(21) Appl. No.: 16/933,383

(22) Filed: Jul. 20, 2020

(65) Prior Publication Data

US 2020/0367738 A1 Nov. 26, 2020

Related U.S. Application Data

(63) Continuation of application No. 16/033,941, filed on Jul. 12, 2018, now abandoned.

(30) Foreign Application Priority Data

Jul. 13, 2017 (DE) .......................... 102017115739.5

(51) Int. Cl.
| | |
|---|---|
| *A61B 1/12* | (2006.01) |
| *A61B 90/20* | (2016.01) |
| *G02B 23/24* | (2006.01) |
| *A61B 1/07* | (2006.01) |

(Continued)

(52) U.S. Cl.
CPC .......... *A61B 1/128* (2013.01); *A61B 1/00006* (2013.01); *A61B 1/00009* (2013.01);
(Continued)

(58) Field of Classification Search
CPC .................................................. A61B 1/128
(Continued)

(56) References Cited

U.S. PATENT DOCUMENTS

| 6,524,237 B1 | 2/2003 | McGowan |
|---|---|---|
| 2003/0219207 A1 | 11/2003 | Guy |

(Continued)

FOREIGN PATENT DOCUMENTS

| DE | 1113788 B | 9/1961 |
|---|---|---|
| DE | 10001289 C1 | 10/2001 |

(Continued)

OTHER PUBLICATIONS

German Search Report Application No. 10 2017 115 739.5 Completed: Jan. 15, 2018; dated Jan. 18, 2018 14 Pages.

(Continued)

*Primary Examiner* — Amir Shahnami
(74) *Attorney, Agent, or Firm* — Whitmyer IP Group LLC

(57) ABSTRACT

An imaging medical instrument such as an endoscope, an exoscope or microscope having a shaft, in which an optical fiber bundle extends from the proximal to the distal end for illuminating field and in which a lens system is arranged for transmitting an image of the field. A light source inputs coupling light into the one proximal end of the optical fiber bundle with a multiplicity of selectively actuatable individual light sources arranged in an array-like manner, with a camera for capturing the transmitted image of the field of view and with a control unit for selectively actuating the individual light sources of the light source for adapting the illumination field. Here, the illumination field has a different form to the field of view. The control unit has an apparatus for analyzing the illumination situation, the apparatus being suitable and provided for analyzing the image captured by the camera in respect of changes depending on the selectively actuated individual light sources and for analyzing the field of view relative to the illumination field.

20 Claims, 5 Drawing Sheets

(51) Int. Cl.
  *A61B 1/045* (2006.01)
  *A61B 1/06* (2006.01)
  *A61B 1/00* (2006.01)
  *A61B 90/00* (2016.01)
  *H04N 5/235* (2006.01)
  *G06T 7/70* (2017.01)
  *A61B 1/04* (2006.01)
  *H04N 5/225* (2006.01)
  *G06T 7/90* (2017.01)
  *G02B 26/08* (2006.01)
  *A61B 90/30* (2016.01)

(52) U.S. Cl.
  CPC ...... *A61B 1/00165* (2013.01); *A61B 1/00172* (2013.01); *A61B 1/00183* (2013.01); *A61B 1/042* (2013.01); *A61B 1/045* (2013.01); *A61B 1/063* (2013.01); *A61B 1/0669* (2013.01); *A61B 1/0684* (2013.01); *A61B 1/07* (2013.01); *A61B 90/20* (2016.02); *A61B 90/361* (2016.02); *G02B 23/243* (2013.01); *G02B 23/2469* (2013.01); *G02B 23/2484* (2013.01); *G06T 7/70* (2017.01); *H04N 5/2256* (2013.01); *H04N 5/2354* (2013.01); *A61B 2090/306* (2016.02); *A61B 2090/309* (2016.02); *A61B 2090/3614* (2016.02); *G02B 26/0833* (2013.01); *G06T 7/90* (2017.01); *G06T 2207/10056* (2013.01); *G06T 2207/10068* (2013.01); *G06T 2207/10152* (2013.01); *G06T 2207/30244* (2013.01); *H04N 2005/2255* (2013.01)

(58) Field of Classification Search
  USPC .......................................................... 348/69
  See application file for complete search history.

(56) References Cited

U.S. PATENT DOCUMENTS

| | | |
|---|---|---|
| 2005/0140270 A1 | 6/2005 | Henson et al. |
| 2005/0267328 A1 | 12/2005 | Blumzvig et al. |
| 2005/0276553 A1 | 12/2005 | Kazakevich |
| 2006/0171693 A1 | 8/2006 | Todd et al. |
| 2006/0256431 A1* | 11/2006 | Hoeg .................. A61B 1/0607 359/435 |
| 2009/0116260 A1 | 5/2009 | Rovegno |
| 2010/0182405 A1 | 7/2010 | Monteiro |
| 2010/0217080 A1* | 8/2010 | Cheung ............. A61B 1/00142 600/121 |
| 2011/0001431 A1 | 1/2011 | Brukilacchio |
| 2011/0257483 A1 | 10/2011 | Mizuyoshi et al. |
| 2015/0185414 A1* | 7/2015 | Baumann ........... A61B 1/00006 362/553 |
| 2017/0078583 A1* | 3/2017 | Haggerty ........... H04N 5/23296 |

FOREIGN PATENT DOCUMENTS

| | | |
|---|---|---|
| DE | 102007063262 A1 | 6/2009 |
| DE | 102008033506 A1 | 1/2010 |
| DE | 102010013307 A1 | 9/2011 |
| DE | 102010033427 A1 | 2/2012 |
| DE | 102010054666 A1 | 6/2012 |
| DE | 102011054031 A1 | 10/2012 |
| DE | 102014107572 A1 | 12/2015 |
| DE | 102013113511 A1 | 6/2018 |
| EP | 2143374 A1 | 1/2010 |
| EP | 2263519 A2 | 10/2010 |
| EP | 2446810 A1 | 5/2012 |
| GB | 2339926 A | 2/2000 |
| JP | 2002102163 A | 4/2002 |
| WO | 0123913 A2 | 4/2001 |

OTHER PUBLICATIONS

European Search Report Application No. 14194853.9 Completed: Apr. 16, 2015 5 Pages.

U.S. Office Action U.S. Appl. No. 16/033,941 dated Mar. 20, 2020 18 Pages.

U.S. Office Action U.S. Appl. No. 16/033,941 dated Oct. 8, 2019 19 Pages.

* cited by examiner

IMAGING MEDICAL INSTRUMENT SUCH AS AN ENDOSCOPE, EXOSCOPE OR MICROSCOPE

CROSS-REFERENCE TO RELATED APPLICATIONS

This application is a continuation of U.S. patent application Ser. No. 16/033,941, filed on Jul. 12, 2018, which in turn claims priority from German Patent Application No. 10 2017 115 739.5, filed on Jul. 13, 2017. The entire content of the priority applications is fully incorporated by reference herewith.

TECHNICAL FIELD

The invention relates to an imaging medical instrument such as an endoscope, exoscope or microscope.

BACKGROUND

The German patent DE 1113788 B has disclosed an endoscope which exhibits a detached light source, the light of which is coupled into the endoscope by a light guide and guided from the proximal end of the endoscope with the eyepiece to the distal end of the endoscope. In the process, the endoscope is typically in a body cavity and emits the supplied light there in a single direction for the purposes of illuminating the body cavity. The significant heat produced by the detached light source cannot lead to injury to the patient as a result of detaching the light source. Furthermore, the handling of this endoscope is found to be comfortable since the heat loss of the light source does not lead to noticeable heating of the endoscope.

The laid-open application DE 10 2011 054 031 A1 has disclosed an exoscope that serves to observe and illuminate an object field on a patient from a location distant from the body of the patient. By way of a detached light source, the light for illumination purposes is supplied to the exoscope via an optical fiber cable and transmitted with the aid of optical fibers to the distal end with the head part in the exoscope, where said light is used for illuminating the object field. Here, there are two exit openings for the light at the head, into which two partial bundles of the optical fiber bundle arranged in the exoscope open.

DE 10 2007 063 262 A1 has disclosed an illumination apparatus for producing light for endoscopy or microscopy. In order to avoid the problems of the light source heating up, said light source having an array of LEDs, said illumination apparatus exhibits a plurality of cooling apparatus using heat pipes. This cooling is found to be very complicated.

Endoscopes with a variable, adjustable viewing direction are known from EP 2 263 519 A2 and EP 2 446 810 A1. Here, the viewing direction is varied by modifying the position or orientation of individual optical elements of the lens systems. These endoscopes require an accurately fitting illumination of the region that is viewed depending on the set viewing direction. In the process, two options are presented. Firstly, the entire possible viewing region is illuminated over a large area. Secondly, it is proposed not only to selectively choose the viewing direction but also, additionally and parallel thereto, to selectively adapt the illumination direction by virtue of co-pivoting a light guide at the distal end of the endoscope and thereby modifying the illumination direction. This solution is found to be very complicated from a mechanical point of view and requires a significant volume in the region of the distal end, said significant volume significantly restricting the introduction of such a variable illumination in the case of endoscopes with a small tube diameter. The problem of the heat load in the region of the light source clearly becomes apparent in the case of a large-area illumination.

An alternative type of endoscope with a variable adjustable viewing direction is known from the German patent application DE 10 2014 107 572 A1 or the European patent EP 2 143 374 B1. In these, an electronic selection of the image data in the style of an electronic zoom or in the style of a laterally displaced selection of the image data of the large-area CCD chip is undertaken on the basis of a field of view that is widened by a wide-angle lens. These endoscopes regularly exhibit a large-area illumination of the field of view, which regularly goes beyond the field of view that was widened by a wide-angle lens. As a result, significant amounts of heat are introduced into the body cavity during an operation, which may lead to injury of the tissue.

The German patent application DE 10 2013 113 511 A1 has disclosed an endoscope, an exoscope or a microscope that, with the aid of a test arrangement, ascertains an assignment function of the proximal ends of optical fibers to the distal ends of the optical fibers in order to reduce the heat influx by input coupling of light into a selection of proximal ends of optical fibers. This endoscope, exoscope or microscope is very complicated in terms of handling.

SUMMARY

The invention is based on the object of specifying an imaging medical instrument such as an endoscope, an exoscope or a microscope that is improved over the prior art, simple to handle and distinguished by a low heat load on the patient.

This object is achieved by an imaging medical instrument such as an endoscope, an exoscope or a microscope, according to the invention.

Advantageous configurations of the invention are the subject matter of the dependent claims.

The imaging medical instrument according to the invention relates to an endoscope, exoscope or microscope having a shaft, in which an optical fiber bundle extends from the proximal end of the shaft to the distal end of the shaft for illuminating the illumination field in the region of the distal end of the shaft and in which a lens system is arranged for transmitting an image of the field of view from the distal end of the shaft to the proximal end of the shaft.

It furthermore exhibits at least one light source for input coupling light into the one proximal end of the optical fiber bundle, wherein the light source is provided with a multiplicity of selectively actuatable individual light sources arranged in an array-like manner. Moreover, it exhibits a camera for capturing the transmitted image of the field of view and a control unit for selectively actuating the individual light sources of the light source for adapting the illumination field to the field of view, wherein the illumination field has a different form to the field of view.

According to the invention, the control unit has an apparatus for analyzing the illumination situation, said apparatus being suitable and provided for analyzing the image captured by the camera in respect of changes depending on the selectively actuated individual light sources and for analyzing the field of view relative to the illumination field.

Within the scope of the analysis, it becomes possible to determine whether and, if so, which parts of the illumination field belong to the field of view and which do not. According to the invention, this knowledge renders it possible to actuate individual light sources of the at least one light source with the aid of the control unit in such a way that the region of the illumination field that corresponds to the field of view or that is congruent therewith is illuminated more strongly than the region outside of the common region. This leads to a restriction in the heat energy introduced at the distal end of the shaft and, as a result thereof, allows a very efficient illumination with a significantly reduced risk of damage or injury to the tissue in the body cavity of the patient.

On account of the analysis of the field of view relative to the illumination field according to the invention, it is possible to attenuate the illumination outside of the common region and thereby provide the option of reducing the risk of injury, even if it still is possible to illuminate the entire possible illumination field over its whole area or beyond the field of view with full strength and obtain maximum illumination in the body cavity thereby. Consequently, according to the invention, the analysis of the common region provides the option of selectively reducing the illumination and thereby reducing the heat influx without substantial impairment in the image quality.

According to a preferred development of the invention, the apparatus for analyzing the illumination situation of the imaging medical instrument is suitable and provided for determining the common region of the field of view and illumination field and, dependent thereon, for directly or indirectly actuating the light source such that the common region is illuminated more strongly than the region outside of the common region. According to the invention, this renders it possible to successfully reduce the heat influx by way of an illumination of the region outside of the common region, which is substantially formed by the overlap between the illumination field and the field of view, and thereby to ensure a differentiated and efficient illumination of the field of view. Here, the differentiated illumination is preferably effectuated with the aid of the control device for actuating the individual light sources.

In addition to the option of illuminating the region outside of the common region with no illuminance or an attenuated, constant, uniform illuminance and thereby achieving a reduced heat influx in a simple manner, it was found to be particularly advantageous to illuminate the region outside of the common region in such a way that it is provided with an illumination gradient such that the illuminance at least substantially reduces with increasing distance from the edge of the common region (gradient region). As a result of this, stray light from a relevant region near the common region is successfully reflected from outside of the common region into the common region and can be captured by the camera.

By contrast, stray light from more distant regions is not reflected from the common region into the relevant field of view due to lack of illumination and, according to this invention, a relevant, damaging heat influx is prevented at the same time.

Here, the gradient region need not necessarily exhibit a continuously falling illuminance or brightness. Individual restricted regions with a constant or with an increasing illuminance or brightness are found to be not bothersome in a relevant fashion.

Not illuminating substantial regions of the illumination field outside of the common region and, as a result, preventing any heat influx has proven its worth in this case.

A particularly preferred embodiment of the invention exhibits a control unit that is suitable and provided for actuating the individual light sources or groups of individual light sources of the light source sequentially for the purposes of analyzing the illumination situation and thereby providing the option of analyzing the effect of the individual light sources or groups of individual light sources on the illumination field in view of the field of view and consequently in view of the common region. The sequential analysis allows very reliable information about the relevance of the activated individual light source or the group of the individual light sources to be successfully obtained, without requiring complicated and cumbersome image analysis systems.

An attribute that marks the individual light source or the group of individual light sources as belonging to the common region and consequently as being of direct importance to the illumination of the field of view is preferably produced within the scope of the sequential analysis. These individual light sources attributed thus or the attributed groups of individual light sources are actuated in a targeted manner, and hence activated, with the aid of the control unit within the scope of normal use of the medical instrument. This successfully allows the common region to be illuminated efficiently and hence with relatively low heat influx, and the facilitation of a good image capture.

A particularly preferred embodiment of the apparatus according to the invention for analyzing the illumination situation is suitable and provided for capturing color changes and/or brightness changes in the captured image when the illumination is modified. Depending thereon, an analysis is carried out as to whether the activated individual light source or group of individual light sources has a relevant influence on the illumination of the common region, i.e., of the overlap of illumination field and field of view. Precisely the brightness change, in addition to the color change, constitutes a very reliable measure for the relevance, and hence the belonging, to the common region. Alternatively, the analysis of the color composition of the field of view has proven its worth as a meaningful variable, wherein the combination of brightness change and color change allows exceedingly reliable information in respect of relevance to be obtained.

Here, the apparatus for analyzing the illumination situation is preferably suitable and provided for determining the common region on the basis of color changes and/or brightness changes that are greater than predetermined thresholds. Here, the threshold, or thresholds, are embodied as an adjustable threshold in particular. A simple analysis is facilitated by the provision of comparisons with threshold values and the option of ensuring an improved analysis of the common region in different operating situations is created by the provision of adjustable threshold values. There is a significant difference in the color changes or brightness changes depending on the type of operation and hence on the type of body cavity in which the medical instrument is used or depending on the type of the respectively employed light source or the employed camera.

It has also proven its worth to embody according to the invention not only medical instruments for a static, unchanging field of view but precisely to develop according to the invention those medical instruments whose field of view has a variable embodiment and thereby facilitate an optimization of the illumination situation in view of the field of view or the analyzed common region. Medical instruments that have a variable embodiment in respect of the viewing direction and/or in respect of the viewing angle and/or in respect of the field of view design, in particular, can facilitate a good image reproduction with an efficient illumination as a result of the analysis according to the invention.

Examples of medical instruments with a variable viewing direction are so-called swing prism endoscopes, be it with a swing optical unit that facilitates variable viewing directions or be it with a digital swing optical unit that facilitates different viewing directions by way of appropriate image processing. Examples of medical instruments with variable viewing angles are zoom microscopes or zoom endoscopes, which can adapt the image portion, and hence the viewing angle, by way of optical or electronic components.

Additionally, there are examples of medical instruments with a variable field of view design, which are able to vary the design of the field of view, for example from a circular cross section to an elliptical cross section and vice versa, or which rotate the elliptical cross section in terms of its orientation. The combination of these various options of varying the field of view is also possible and preferably selected as a trigger for the analysis of the illumination situation according to the invention.

Here, it was found to be particularly useful to embody the apparatus for analyzing the illumination situation in such a way that an analysis of the illumination situation is initiated or carried out if there is a change in the field of view or in the illumination field. This very reliably successfully renders it possible to efficiently adapt the illumination field to the modified field of view and facilitate an efficient illumination with little risk of injury. According to the invention, the temporal scope of the analysis can be kept short.

Moreover, it was found to be particularly advantageous to embody the apparatus for analyzing the illumination situation in such a way that an analysis of the illumination situation is undertaken upon start up of the medical instrument.

Additionally, it has also proven its worth to undertake a regular analysis of the illumination situation, in particular during the running operation of the medical instrument according to the invention at fixed time intervals. An adaptation of the illumination to the respective current field-of-view situation is facilitated on the basis of the analysis, wherein there regularly is a change in the illumination situation or in the field-of-view situation, especially at start up, said change demanding an adaptation in view of an efficient illumination. The regular checks can moreover capture and take account of changes in the operating situation and thereby ensure a particularly reliable illumination with a low risk of injury.

Preferably, individual light sources are embodied as LEDs, OLEDs, diode lasers and/or supercontinuum lasers. These facilitate a very compact and bright construction of the medical instrument. Further, the combination of different individual light sources, which can be operated together in groups, has also proven its worth since, in this case, the different properties of the individual light sources, particularly in view of the different illuminance or frequency responses, come to bear to particular extent.

According to a preferred development of the medical instrument according to the invention, the light source has at least one scanning laser light source, the laser beam of which, in particular, is deflected in scanning fashion by way of a MEMS (micromirror—micro-electromechanical system). This embodiment of the light source facilitates a very compact construction, which, moreover, can very efficiently illuminate the analyzed common region in scanning fashion and can thereby very advantageously reduce the heat introduced into the body cavity.

In addition, it has proven its worth to provide at least one beam-widening optical element distally upstream of the distal end of the light guide bundle. As a result of this, the field of view can be successfully illuminated very efficiently and the heat influx according to the invention can be successfully kept low, particularly when using a digital zoom or digital pivot optical unit. In particular, cone-shaped tapers or beam-widening lenses or microlens systems or Fresnel lenses have particularly proven their worth as beam-widening optical elements.

In a preferred development, the beam-widening optical element or elements is/are arranged not only distally upstream of the end or ends of the optical fiber bundle or bundles, but also upstream of the distal front lens of the lens system for image transmission. This facilitates a compact construction of the distal end of the medical instrument and protects the components of the medical instrument lying therebehind.

BRIEF DESCRIPTION OF THE DRAWINGS

Below, the invention will be explained in an exemplary manner on the basis of preferred exemplary embodiments, with reference being made to the figures. The invention is not restricted to these preferred exemplary embodiments.

DETAILED DESCRIPTION

Figure 1:
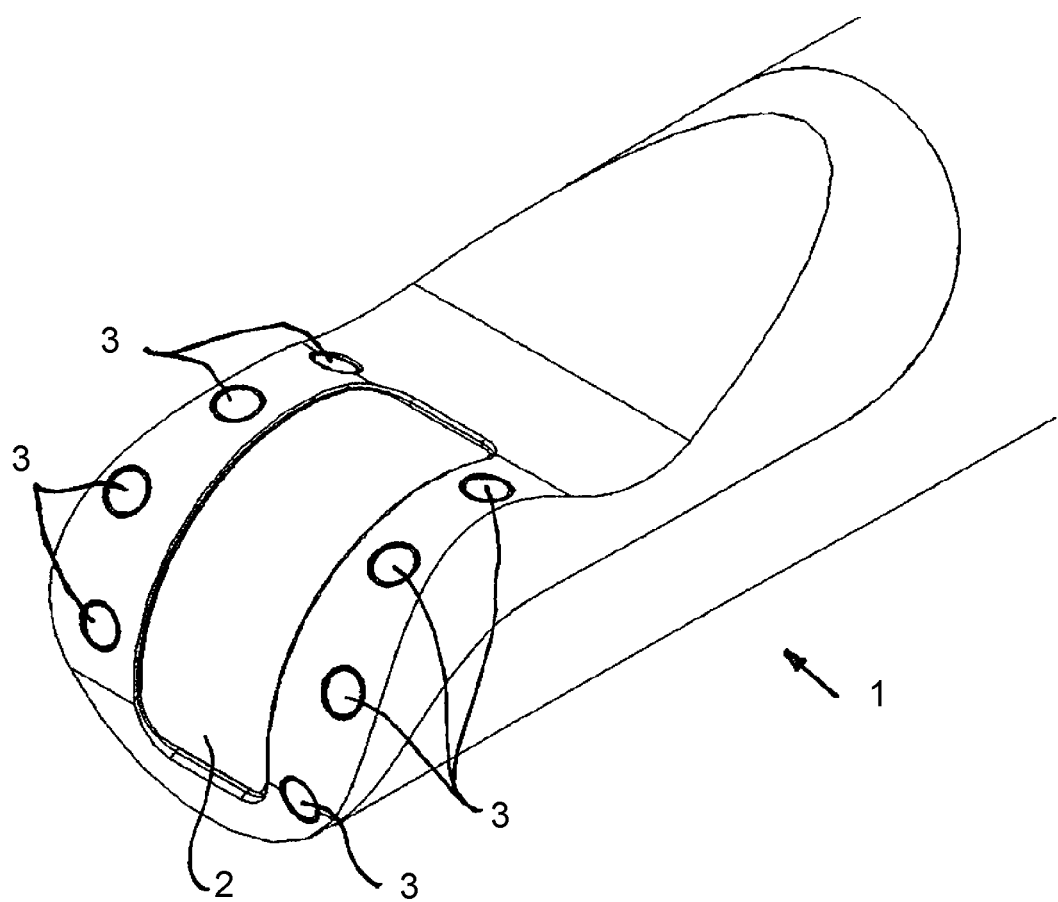
FIG. 1 shows a schematic illustration of an exemplary distal end of an endoscope with a variable viewing direction.

FIG. 1 shows, in an oblique view, the schematic construction of an exemplary distal end 1 of an endoscope 10 according to the invention or the distal end 1 of the endoscope shaft. The observation window 2, which has an elongate embodiment and which is arranged centrally in the region of the distal end 1, can be identified centrally. Here, the observation window 2 has an arched embodiment and a substantially rectangular design with a substantially cylindrically arched embodiment. The observation window 2 is formed by the distal front lens of the lens system of the endoscope 10 according to the invention. Light-exit openings 3 are arranged along the longitudinal extent of the observation window 2. Here, this relates to a total of eight light-exit openings 3, in which a partial bundle 13 of the optical fiber bundle 11 for transmitting light from the proximal end 2 to the distal end 1 of the endoscope 10 opens in each case. At the distal end 1, the partial bundles 13 are adhesively bonded to one another in such a way in the light-exit openings 3 that the light-exit openings have a gas-tight and liquid-tight, and hence autoclavable, embodiment. Here, the partial bundles 13 of the light-exit openings 3 point in different directions into the activity region of the endoscope 10. Consequently, the various light-exit openings 3 provide the option of illuminating different spatial regions in the activity region of the endoscope 10.

The endoscope 10 is suitable for varying the field of view 16 with the aid of an adjustment element 11 for the viewing direction 17. By actuating the adjustment element 11, a prism in the region of the distal end 1 of the endoscope shaft of the lens system for transmitting the image is modified in terms of its position or orientation in such a way to this end that the field of view 16 is varied in terms of the viewing direction 17. Here, the field of view 16 is captured by the observation window 2.

Figure 2:
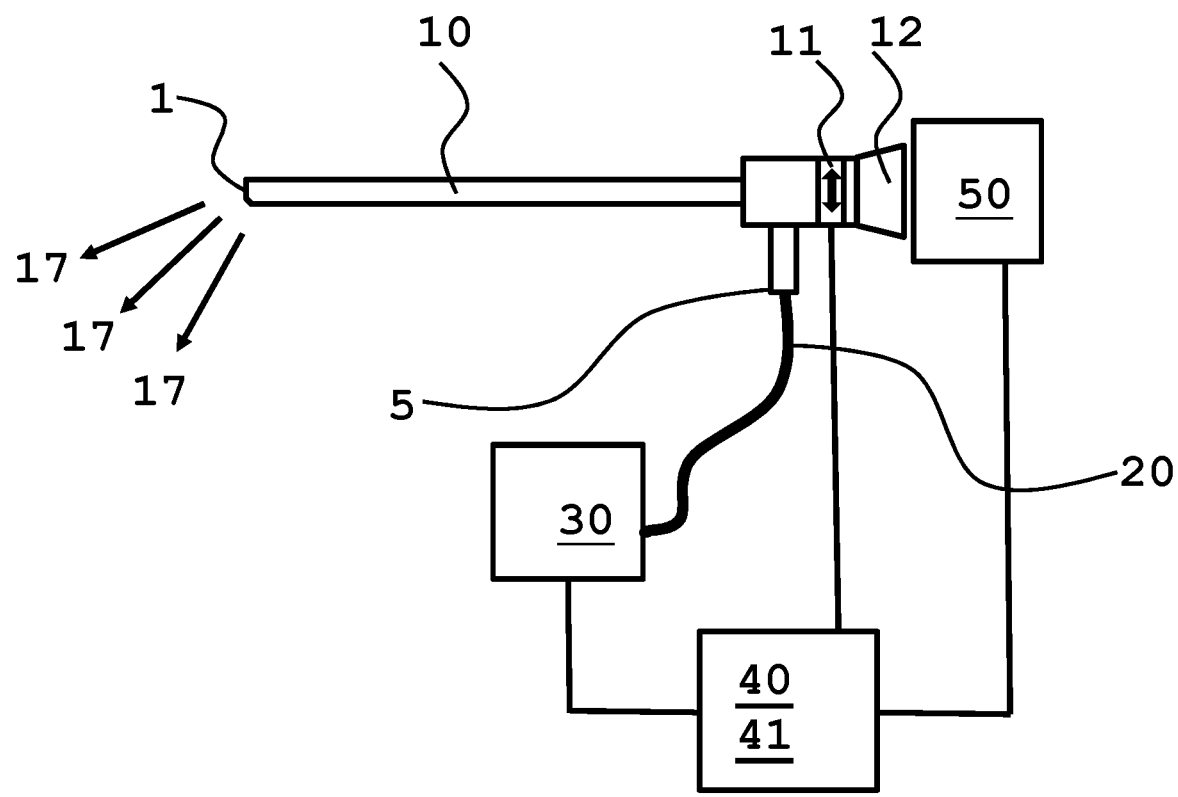
FIG. 2 shows a schematic illustration of a construction of an exemplary endoscope according to the invention.

FIG. 2 schematically illustrates the construction of an exemplary endoscope 10 with a shaft. The shaft extends from the distal end 1 up to the eyepiece 12 or up to the proximal end 5. The proximal end 5 is adjoined by a light guide cable 20, which is connected to the light source 30 and into which light of the light source 30 is input coupled and guided to the endoscope 10. There, the light is coupled by the proximal end 5 into an optical fiber bundle 8, which extends from the proximal end 5 to the distal end 1 of the shaft. Consequently, the light produced by the light source 30 is guided via the light guide cable 20 and the optical fiber bundle 8 to the distal end 1, where it emerges from the endoscope 10 and illuminates the region that is distal to the endoscope 10. The illuminated region forms the illumination field 15.

Moreover, the shaft of the endoscope 10 exhibits a lens system for transmitting an image of the field of view 16 from the distal end 1 to the eyepiece 12. The eyepiece 12 is adjoined by a camera 50. The camera 50 captures the transmitted image of the field of view 16.

The field of view 16 can be varied by virtue of being able to pivot the viewing direction 17.

The field of view 16 differs from the illumination field 15 in terms of dimensions and in terms of form. The field of view 16 changes relative to the illumination field 15 by varying the viewing direction 17.

The light source 30 is provided with a multiplicity of selectively actuatable individual light sources that are arranged in an array-like manner, it being possible to actuate said individual light sources individually or in groups 7 with the aid of a control unit for selective actuation in such a way that the illumination field 15 can be varied.

According to the invention, this is effectuated in such a way that the illumination field 15 is not irradiated with the full light output over the entire area thereof, but that regions, which are determined in a differentiated manner, of the illumination field 15 are irradiated more strongly or less strongly. Which regions are irradiated more strongly or less strongly is determined by an apparatus 41 for analyzing the illumination situation, said apparatus being part of the control unit.

As part of the control unit 40, the apparatus 41 for analyzing the illumination situation is connected to the camera 50 and the adjustment element 1 for the purposes of setting the viewing direction 17.

Here, the analysis of the illumination situation is effectuated by virtue of the individual light sources or the groups 7 of individual light sources being individually activated or deactivated sequentially, i.e. step-by-step, and the change of the image captured by the camera 50 being analyzed in the process.

If the camera 50 captures a brightness change that is greater than a predetermined first brightness threshold, this is interpreted as confirmation that this current activated individual light source or this group 7 of individual light sources illuminates a portion of the illumination field 15 that is part of the field of view 16. This individual light source or this group 7 of individual light sources is marked by virtue of having assigned to it an attribute, for example "relevant to the illumination of the field of view".

After completion of the analysis of all individual light sources or groups 7 of individual light sources, all individual light sources or groups 7 of individual light sources that illuminate the field of view are captured and provided with the specific attribute. With the aid of the attribute, it is possible to activate the individual light sources or the groups 7 of individual light sources according to the invention in a targeted and selective manner and efficiently ensure an illumination of the field of view.

Here, individual light sources without this attribute are not activated or only activated in an attenuated fashion such that only the overlapping region (common region) of field of view 16 and illumination field 15 is illuminated strongly during the normal operational state, while the region outside of the overlapping region is illuminated in a significantly weaker fashion or not at all.

According to the invention, this renders it possible to restrict the heat influx as a result of the light source into the body cavity in which the activity field of the endoscope lies and, as a result, this renders it possible to reduce injury to the tissue. This is successful without there being a relevant deterioration in the image quality as a result of the restricted illumination by the light source 30.

According to the invention, determining whether or not the portion of the illumination field 15 that is irradiated by the activated individual light source or by the group 7 of individual light sources is captured by the camera 50 and hence whether or not it is part of the field of view 16 is successful. The overlap between the field of view 16 and the illumination field 15 is referred to as common region 18. It represents the region of the illumination field 15 that is captured by the camera 15 as a field of view 16, and, conversely, the part of the field of view 16 that is illuminated by the light source 30.

In addition to the predetermined first brightness threshold for determining the common region, it has also proven its worth to provide a second, lower brightness threshold. This second brightness threshold typically lies in the region of 50% of the value of the first brightness threshold. As a result of this additional second brightness threshold, dividing the region outside of the common region 18 into two parts is successful; to be precise, into a region that, in the case of illumination by way of reflected light or stray light, exhibits a not insignificant influence (brightness change above the second threshold but below the first threshold) and a region with an insignificant influence (brightness change below the second threshold).

The region that, in the case of illumination by reflected light or stray light, exhibits a not insignificant influence is preferably illuminated in a weaker fashion during the normal operational state than the common region. In particular, it exhibits an illumination gradient that exhibits a regularly weaker illumination with increasing distance from the common region. This region is referred to as gradient region 19.

By contrast, the region with the insignificant influence is not illuminated at all in the normal operational state; the associated individual light sources or groups 7 of individual light sources are not activated.

Hence, it is clear that the endoscope 10 according to the invention can be operated in two states of operation: the normal operational state, in which at least the common region 18 is illuminated strongly and captured with the aid of the camera 50, and the analysis state, in which the illumination situation is analyzed and hence the common region 18 is adapted and the individual light sources or groups 7 of individual light sources that are relevant for the illumination of the common region 18 are ascertained.

Here, the analysis state is initiated by a change in the field of view 16, in particular in the viewing direction 17. The change in the viewing direction 17 is captured by the control unit 40 by way of the change in the position of the adjustment element 11 for the viewing direction 17 at the endoscope 10. This ensures that a change in the field of view 16 always brings about monitoring and adaptation of the illumination situation. Consequently, an efficient illumination is regularly ensured in the case of reduced heat influx.

Additionally, it has proven its worth to initiate an analysis of the illumination situation as soon as the endoscope 10 is started up.

Below, the analysis state is preferably started at intervals after a predetermined time has elapsed. As a result of this, it is possible to take account of changes in the illumination situation caused by external conditions, for example by a change in the operation situation, such as a substantial change in the tissue to be operated.

Figure 3:
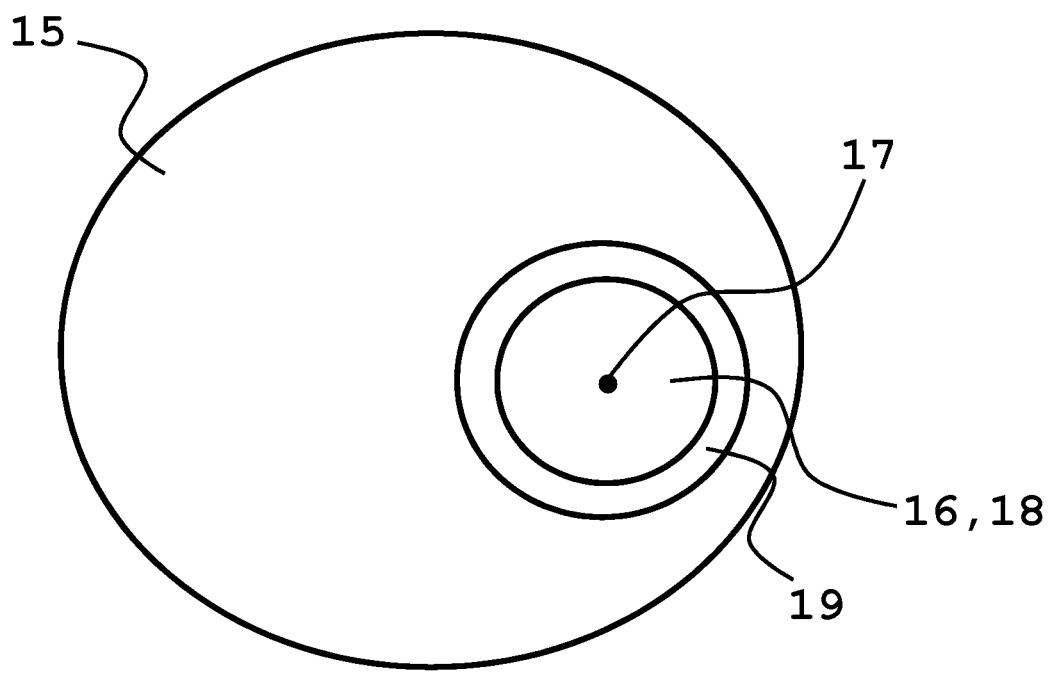
FIG. 3 shows an exemplary arrangement of a field of view in relation to an illumination field of the endoscope according to FIG. 2.
Figure 4:
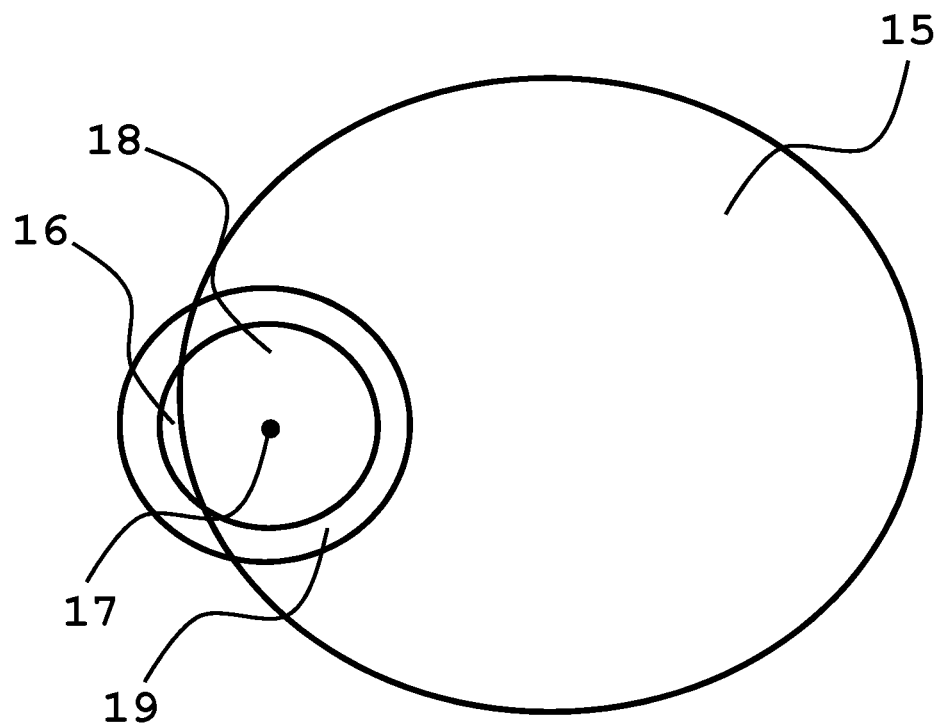
FIG. 4 shows another exemplary arrangement of a field of view in relation to an illumination field of the endoscope according to FIG. 2

FIG. 3 and FIG. 4 schematically illustrate different situations, in which the illumination field 15 and the field of view 16 are illustrated. The illumination field 15 exhibits an elliptical form and comprises a large region that can be illuminated with the aid of individual light sources. The field of view 16 exhibits a circular form and can be varied by changing the viewing direction 17.

FIG. 3 shows a situation in which the viewing direction 17 lies in the right region of the illumination field 15. The field of view 16 surrounds the viewing direction 17 and lies completely within the illumination field 15, and so the field of view 16 simultaneously forms the common region 18. In the operational state, the common region 18 is illuminated in the entirety thereof and strongly.

The gradient region 19 surrounds the common region 18 and it is illuminated in a weaker fashion than the common region 18. The illumination field 15 that is not part of the common region 18 or the gradient region 19 is not illuminated, and so the heat influx is significantly reduced without, according to the invention, the illumination of the field of view 16 and the image reproduction of the endoscope 10 being significantly impaired.

The viewing direction in FIG. 4 is displaced to the left relative to FIG. 3. The field of view 16 protrudes beyond the illumination field 15, and so the common region 18 is smaller than the field of view 16. Therefore, according to the invention, only part of the field of view 16, i.e. the common region 18, is illuminated in full in the operational state. This applies in a corresponding manner to the gradient region 19. Consequently, according to the invention, the avoidance of an unnecessary heat influx is successful.

Figure 5:
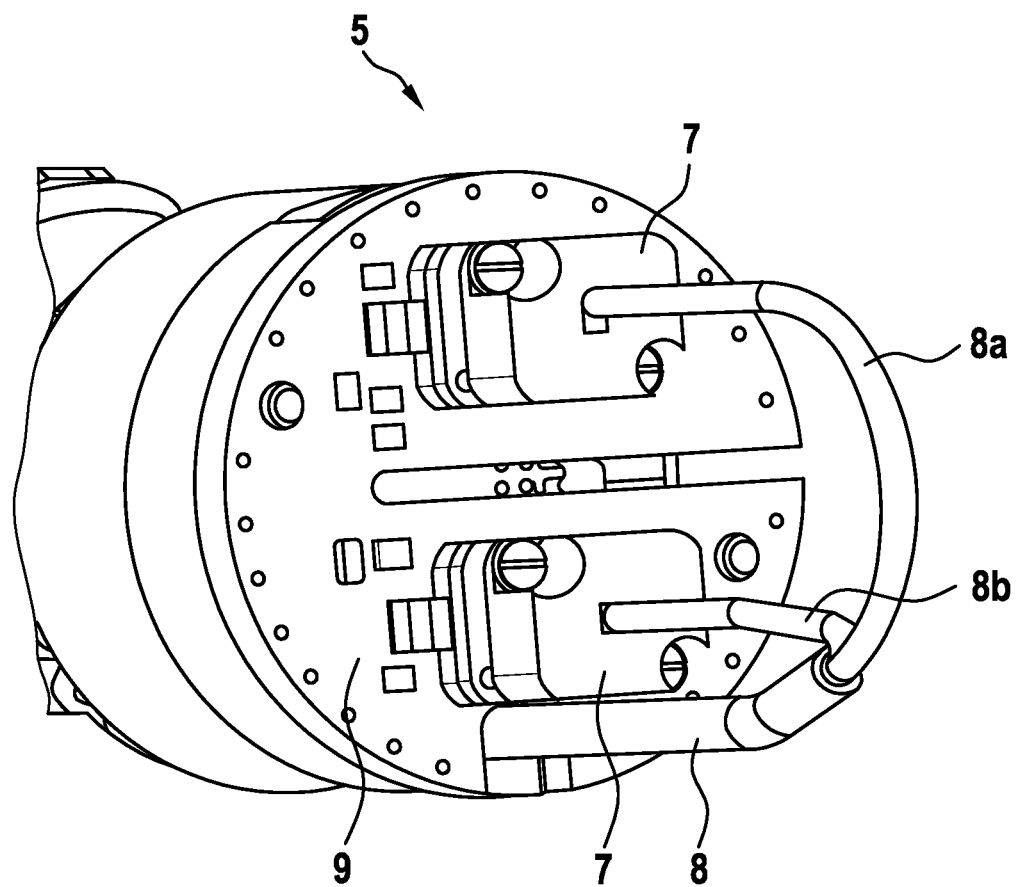
FIG. 5 shows a schematic illustration of an exemplary proximal end of an endoscope with a variable viewing direction.

FIG. 5 schematically illustrates an alternative embodiment of the endoscope 10. Contrary to the light source 30 of FIG. 2, which represents a detached, cold light source 30, the groups 7 of individual light sources, which form the light source 30, are arranged at the proximal end 5 of the shaft of the endoscope 10 on a circuit board 9. The circuit board 9 exhibits electronic circuits for controlling the groups 7 of individual light sources. The groups 7 of individual light sources embodied as LEDs produce light that is input coupled into partial fiber bundles 8a, 8b, which open into the optical fiber bundle 8. The optical fiber bundle 8 extends from the proximal end 5 to the distal end 1 and transports the produced light through the endoscope 10 to the illumination field 15. This arrangement is found to be very compact and very illumination-efficient.

The invention claimed is:

1. A method for imaging, comprising:
providing an imaging instrument including:
a shaft;
an optical fiber bundle extending between a proximal end and a distal end of the shaft;
a lens system configured to transmit an image of a field of view from the distal end of the shaft to the proximal end of the shaft;
a light source configured to be coupled to a proximal end of the optical fiber bundle, the light source including a plurality of individual light sources with respective individual illumination fields that collectively define an illumination field of the light source, the illumination field having a different dimension than the field of view; and
a camera configured to capture an image of the field of view after transmission by the lens system; and
an adjustment element configured to be actuated to change the field of view;
actuating the adjustment element to thereby change the field of view relative to the illumination field of the light source;
performing a sequence of steps including:
selectively activating and deactivating the individual light sources of the light source;
detecting changes in the image captured by the camera during the step of selectively actuating and deactivating the individual light sources;
based on the detected changes, identifying individual light sources, among the plurality of individual light sources, that have individual illumination fields overlapping the field of view; and
fully activating all of the identified individual light sources and at least partially deactivating all other individual light sources of the light source;
wherein the detecting step involves detecting color changes in the image captured by the camera.

2. The method of claim 1, wherein the fully activating step involves fully activating all of the identified individual light sources and fully deactivating all other individual light sources of the light source.

3. The method of claim 1, wherein the fully activating step involves fully activating all of the identified individual light sources and selectively deactivating all other individual light sources of the light source such that a region outside of the field of view exhibits illuminance that reduces with increasing distance from the edge of the field of view.

4. The method of claim 1, wherein the fully activating step involves fully activating all of the identified individual light sources and selectively deactivating all other individual light sources of the light source such that regions of the illumination field outside of the field of view are not illuminated.

5. The method of claim 1, wherein the selectively activating and deactivating step involves sequentially activating and deactivating the individual light sources of the light source.

6. The method of claim 1, wherein the detecting step further involves detecting brightness changes in the image captured by the camera.

7. The method of claim 1, wherein the detecting step further involves detecting whether a color change in the image captured by the camera is greater than a predetermined color change threshold.

8. The method of claim 1, further comprising repeating the sequence of steps if there is a change in at least one of the field of view and the illumination field.

9. The method of claim 1, wherein the sequence of steps is performed upon startup of the imaging instrument.

10. The method of claim 1, wherein the sequence of steps is repeatedly performed at predetermined time intervals.

11. The method of claim 1, wherein the light source has a scanning laser light source.

12. The method of claim 1, wherein the imaging instrument includes a radiation-widening optical element distally upstream of the distal end of optical fiber bundle.

13. The method of claim 12, wherein the radiation-widening optical element is arranged distally upstream of a distal front lens of the lens system.

14. The method of claim 1, further comprising an adjustable optical element in a distal end region of the imaging instrument;
wherein actuation of the adjustment element modifies a position and/or an orientation of the adjustable optical element to thereby change the field of view.

15. The method of claim 14, wherein the adjustable optical element is a prism.

16. A method for imaging, comprising:
providing an imaging instrument including:
  a shaft;
  a lens system configured to transmit an image of a field of view from the distal end of the shaft to the proximal end of the shaft;
  a light source configured to be coupled to a proximal end of the optical fiber bundle, the light source including a plurality of individual light sources with respective individual illumination fields that collectively define an illumination field of the light source, the illumination field having a different dimension than the field of view; and
  a camera configured to capture an image of the field of view after transmission by the lens system; and
  an adjustment element configured to be actuated to change the field of view relative to the illumination field of the light source;
selectively activating and deactivating the individual light sources of the light source;
detecting changes in the image captured by the camera during the step of selectively actuating and deactivating the individual light sources;
based on the detected changes, identifying individual light sources, among the plurality of individual light sources, that have individual illumination fields overlapping the field of view; and
fully activating all of the identified individual light sources and at least partially deactivating all other individual light sources of the light source;
wherein the detecting step involves detecting color changes in the image captured by the camera.

17. The method of claim 16, wherein the detecting step further involves detecting brightness changes in the image captured by the camera.

18. The method of claim 16, wherein the detecting step further involves detecting whether a color change in the image captured by the camera is greater than a predetermined color change threshold.

19. The method of claim 16, wherein the detecting step further involves detecting whether a brightness change in the image captured by the camera is greater than a predetermined brightness change threshold.

20. The method of claim 1, wherein the detecting step further involves detecting whether a brightness change in the image captured by the camera is greater than a predetermined brightness change threshold.

* * * * *